Figure 1:
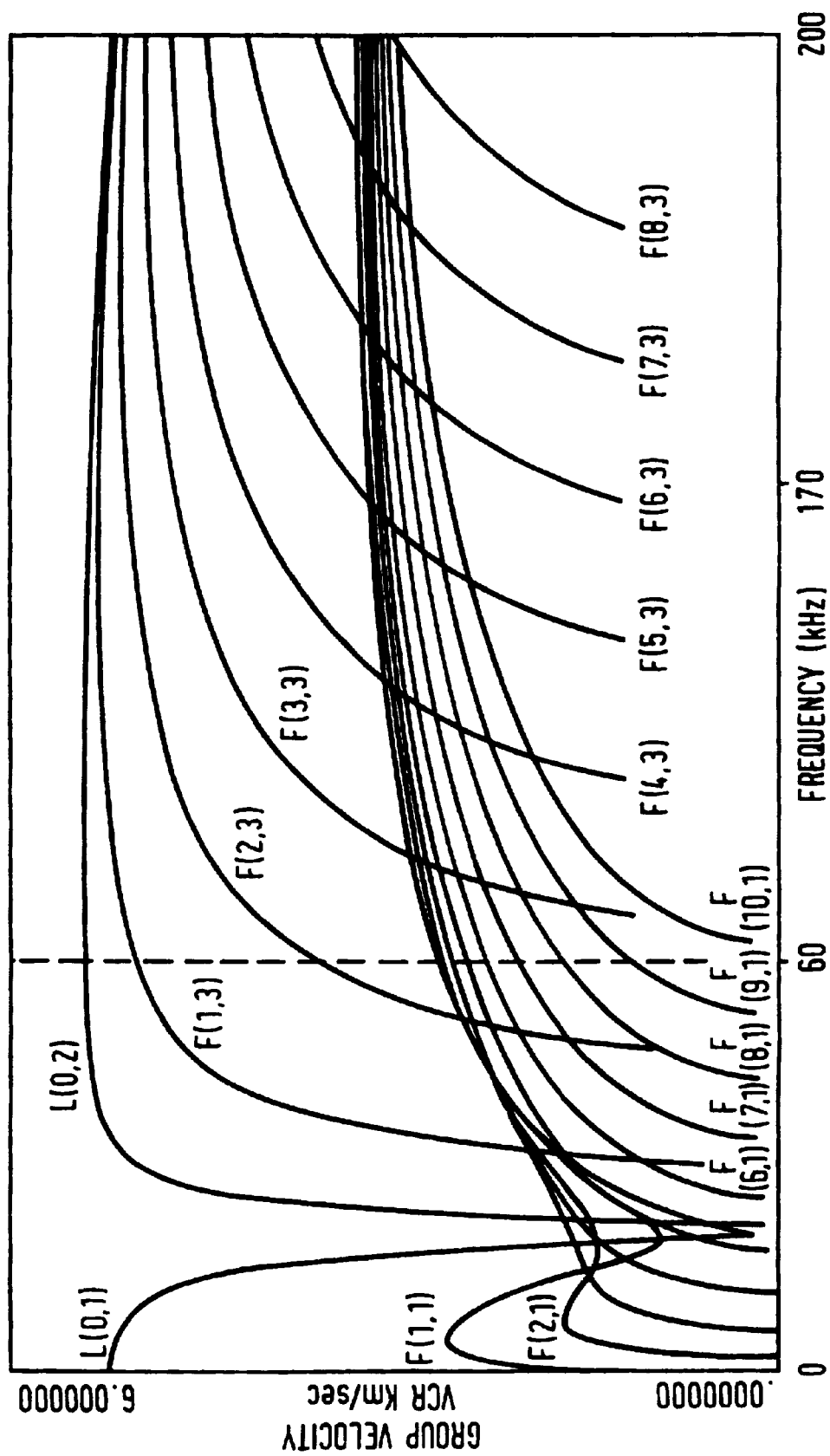

United States Patent

Cawley et al.

[11] Patent Number: 6,148,672
[45] Date of Patent: Nov. 21, 2000

[54] INSPECTION OF PIPES

[75] Inventors: Peter Cawley, London; David Nathaniel Alleyne, Harrow; Che Wan Chan, Orpington, all of United Kingdom

[73] Assignee: Imperial College of Science, Technology of Medicine, London

[*] Notice: This patent issued on a continued prosecution application filed under 37 CFR 1.53(d), and is subject to the twenty year patent term provisions of 35 U.S.C. 154(a)(2).

[21] Appl. No.: 08/836,375

[22] PCT Filed: Oct. 20, 1995

[86] PCT No.: PCT/GB95/02482

§ 371 Date: Sep. 10, 1997

§ 102(e) Date: Sep. 10, 1997

[87] PCT Pub. No.: WO96/12951

PCT Pub. Date: May 2, 1996

[30] Foreign Application Priority Data

Oct. 20, 1994 [GB] United Kingdom .................... 9421187
Aug. 31, 1995 [GB] United Kingdom .................... 9517794

[51] Int. Cl.$^7$ ........................................................ G01N 9/24
[52] U.S. Cl. ......................................................... 73/622
[58] Field of Search ............................ 73/600, 601, 598, 73/622, 628, 623

[56] References Cited

U.S. PATENT DOCUMENTS

| | | | |
|---|---|---|---|
| 4,404,853 | 9/1983 | Livingston | 73/622 |
| 4,660,419 | 4/1987 | Derkaces et al. | 73/622 |
| 5,007,291 | 4/1991 | Walters et al. | 73/622 |
| 5,113,697 | 5/1992 | Schlawne | 73/622 |
| 5,156,636 | 10/1992 | Kuljis | 73/622 |
| 5,520,061 | 5/1996 | Thibault et al. | 73/622 |
| 5,581,037 | 12/1996 | Kwun et al. | 73/622 |
| 5,767,410 | 6/1998 | Lareau et al. | 73/623 |

*Primary Examiner*—Max Noori
*Attorney, Agent, or Firm*—Fay, Sharpe, Fagan, Minnich & McKee, LLP

[57] ABSTRACT

An apparatus and a method for inspecting elongate members, especially pipes, using Lamb waves. The apparatus and method provide for the propagation of an axisymmetric Lamb wave of a single mode in one direction along the pipe. A receiver is provided to receive the Lamb wave after its passage along the pipe and convert the received wave for storage, processing and analysis to determine whether or not there are faults present in the pipe. The apparatus includes at least one and usually several excitation rings each having a plurality of Lamb wave exciters deployed in equiangular spacing in a ring clamping structure whereby each exciter can be pressed with equal force against the surface of the pipe under inspection.

18 Claims, 6 Drawing Sheets

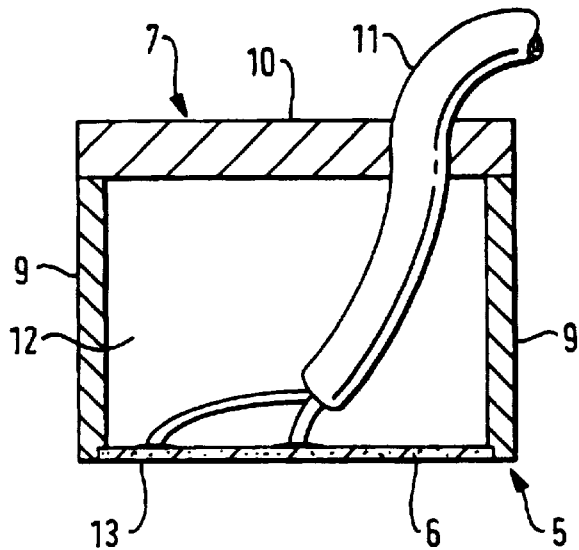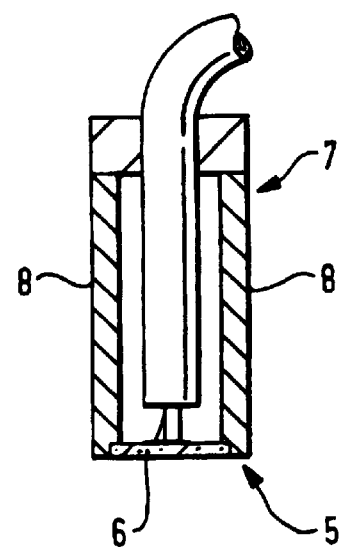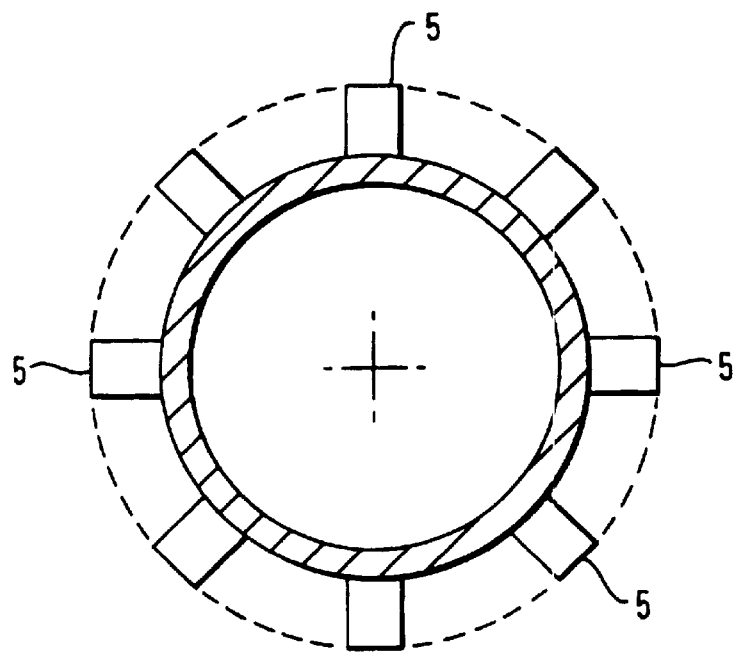

INSPECTION OF PIPES

The present invention is concerned with the inspection of elongate members generally, but especially pipes, rods, beams, struts and other structural members in order to ascertain their condition, especially whether or not they are subject to fatigue, corrosion or erosion. The invention will be particularly described with reference to its industrial application for inspecting pipes but this is not to be construed as a limit of its application.

The inspection of pipe condition for such deleterious effects as corrosion, erosion or fatigue is frequently complicated by the need to shut down plant, the provision of obscuring lagging and the difficulty in imaging the interior of the pipe. Existing techniques for the inspection of pipes include removing any lagging to inspect the pipe visually, and then employing ultrasonic inspectoscopes or the like to look for defects developing on the inside of the pipe. An alternative technique involves mounting an ultrasonic or eddy current probe on a sledge which is then towed along the inside of the pipe. As with the aforementioned external approach every point along the pipe length must be scanned by the probe resulting in very long inspection times.

It is an object of the present invention to provide an apparatus for inspecting the condition of a pipe which alleviates the aforementioned disadvantages of the prior art.

According to one aspect of the present invention there is provided apparatus for inspecting a pipe comprising at least one ring of angularly spaced wave exciters adapted to propagate one of:

(a) a single mode axially symmetric Lamb wave, (b) a single torsional mode wave, (c) a single flexural mode wave, in a single direction along a pipe, receiving means capable of receiving the waves and, analysing means capable of analysing the received wave to assess the condition of the pipe.

Preferably the wave will be an axisymmetric Lamb wave.

The excitation assembly is preferably composed of a first excitation ring which can be secured to the exterior of the pipe wall and controlled to propagate axi-symmetric Lamb waves along the pipe.

The first excitation ring propagates many modes of axi-symmetric Lamb waves in both the forward and reverse directions along the pipe. The signals received by the receiving means using such a simple excitation assembly are extremely difficult to analyse usefully. Accordingly the assembly may advantageously include second and third excitation rings, each of a construction similar to the first excitation ring. The first, second and third excitation rings cooperate to suppress all but a single axi-symmetric mode propagating in a single "forward" direction. If only a single extra excitation ring is included in the excitation assembly the reverse direction propagating waves or the unwanted modes can be suppressed by cooperation of the excitation rings in the assembly. Thus the pipe can be inspected by means of a single axi-symmetric mode Lamb wave propagating in one direction thereby greatly simplifying the analysis of the waveform received by the receiving means.

The axi-symmetric unidirectionally propagating Lamb wave can be received by a receiving means of similar construction to the excitation assembly at a position longitudinally remote from the excitation assembly. However a more convenient and economic receiving means can be provided by wave exciter/transducers of the excitation assembly. In this preferred latter case the waveform received will be a reflection from a structure in the pipe wall. The reflected wave will have been altered by any structure in the pipe wall; such structures may include cracks or deformations which can thus be detected by analysis of the received waveform.

It will be appreciated that under some circumstances the apparatus according to the invention may be used as a permanent installation for frequent or continuous inspection of the pipe condition. However, the apparatus can be adapted to be readily mounted and dismounted for intermittent pipe inspection.

The preferred operating frequency of the Lamb wave will depend upon the size of the pipe but will ordinarily be in the range 10 kHz to 500 kHz. Preferably the fastest propagating mode of Lamb wave will be selected for the inspection.

The excitation of Lamb waves has previously been achieved by the use of exciters comprising electromagnetic acoustic transducers (EMAT's) but EMAT's are too large to be used in the construction of an excitation assembly capable of inducing axi-symmetric Lamb waves in a pipe which will commonly be between 70 mm and 460 mm.

Accordingly a further aspect of the present invention is a wave exciter/transducer characterised in that a piezoelectric element is polarised to deform when a voltage is applied across its faces and has a backing structure engageable by means to clamp the piezoelectric element to the pipe whereby a wave can be propagated in the pipe in response to a control signal and to generate a wave signal in accordance with a wave traveling through the pipe.

In a first possible embodiment of the exciter the piezoelectric element is an expansion type element which expands and contracts longitudinally and the backing structure is provided by a casing filled with a lossy material. The casing and lossy material serves the purposes of protecting electrical connections to the element, providing flexural stiffness to protect the very brittle element when it is pressed onto a rough pipe surface and damping our reverberations so that the Lamb wave exciter outputs a faithful reproduction of the excitation signal.

Experience with the expansion type transducer described above has shown that even when extreme care is taken in setting up the transducers there was a persistent baseline signal of about 1% of that of the mode of interest and setting up to obtain such a low baseline signal meant that a test could take as much as two hours. This is impractical for industrial use.

The aforementioned problem is alleviated by an alternative and preferred embodiment of the exciter wherein the element may be a shear polarised piezoelectric element. In this embodiment the surface of the element which engages the pipe is displaced in only one direction at a time, the direction changing in accordance with the excitation waveform but always parallel to the opposite surface of the element by which it is mounted to the block. The force on the pipe is therefore instantaneously applied in one direction irrespective of the position of contact on the pipe and varying in magnitude and direction in accordance with the waveform applied to the element.

Experience with transducers housed in a casing filled with the lossy material shows that, at the operating frequency of approximately 70 kHz the damping is not adequate and when the transducer is used as a receiver a reverberation tail appears in the response. The extent of this tail varies between different transducers of nominally the same design, making it very difficult to obtain an axially symmetric excitation ring. The cause of the reverberation tail is a resonance of the exciter which frequently occurs between 70 and 80 kHz but may occur at other operating frequencies. The operating frequency of the exciter is about 70 kHz and so causes a major problem.

To alleviate the aforementioned problem the piezoelectric element is backed with a rigid backing which moves all resonance of the transducer beyond the operating frequency range. The rigid backing is preferably a steel backing block and may be applied to either the expansion or shear polarised type of piezoelectric element. A further advantage of this type of backing structure is a reduction in the size of each Lamb wave exciter and it is very robust.

Each excitation ring may be comprised of a plurality of the exciters equally spaced from each adjacent exciter and clamped against a wall of the pipe by the clamping means. Each exciter can act as a wave receiver by converting the mechanical force of the wave passing through the pipe to an electrical signal. Thus the exciter will in some cases be a transducer.

It may be possible to employ an excitation ring comprising a plurality of wave exciter/transducers equiangularly spaced around the pipe under inspection where each exciter is in communication with a corresponding channel of the analysing means so that non-axisymmetric modes of the waves can be received for analysis.

A receiver assembly may be controlled to receive only a single mode of the propagating wave traveling in a single direction.

Figure 2:
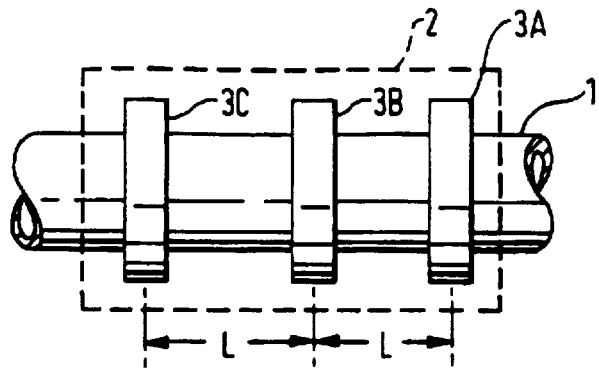
Figure 3:
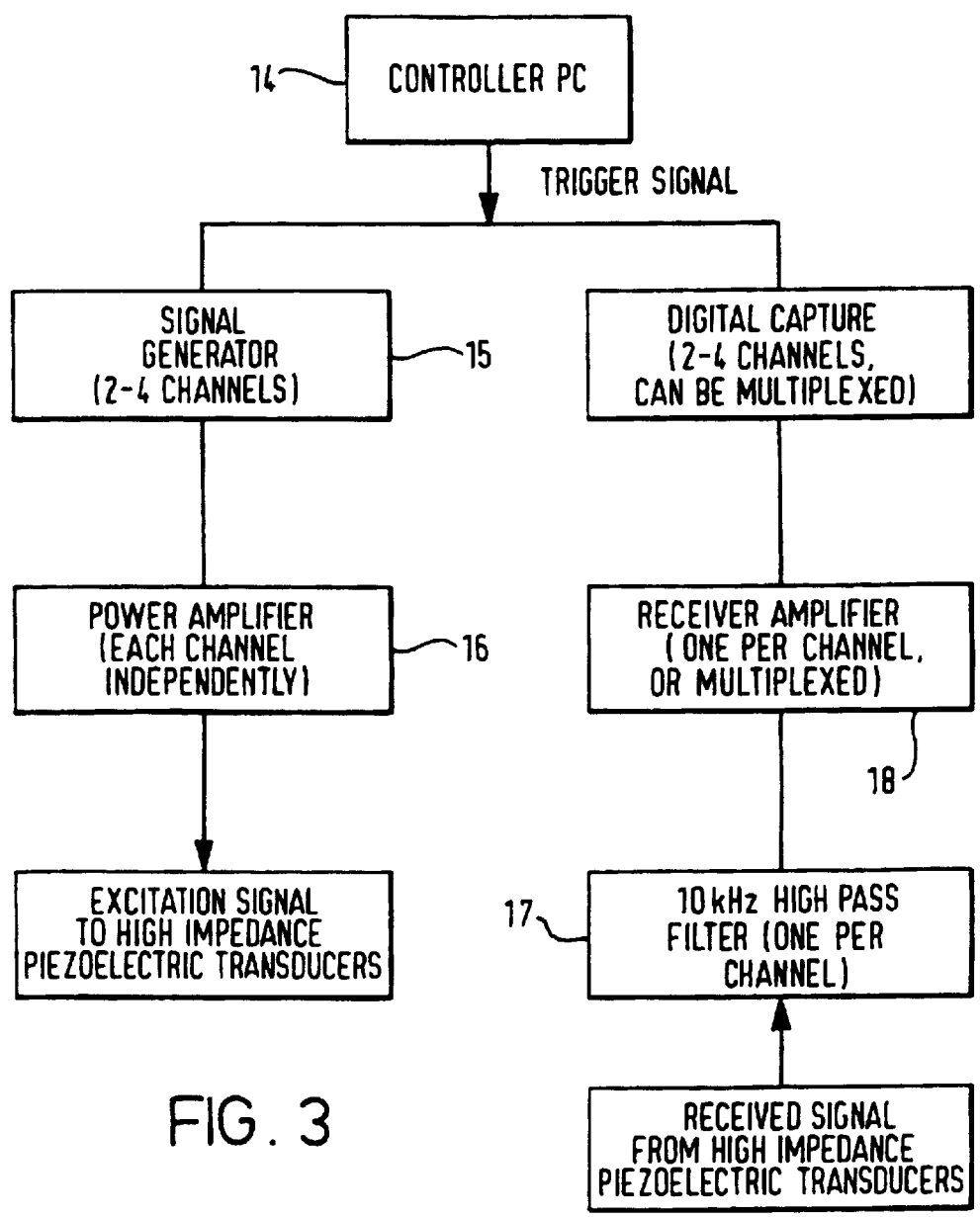

Embodiments of apparatus for inspecting a pipe using Lamb waves and constructed according to the invention will now be described, by way of example only, with reference to the accompanying figures; in which, FIG. 1 shows the group velocity dispersion curves for a pipe having a diameter of 76.2 mm (3 inch) and a wall thickness of 5.5 mm for both axi-symmetric L(*,*) and non axi-symmetric F(*,*) Lamb wave modes propagated along the pipe, FIG. 2 diagrammatically illustrates a Lamb wave excitation assembly clamped to a pipe, FIG. 3 is a block diagram of the apparatus, FIG. 4 is a sectioned elevation of a first embodiment of a single Lamb wave exciter, FIG. 5 is a sectioned end elevation of the Lamb wave exciter in FIG. 4, FIG. 6 is a diagrammatic sectional view through the pipe showing the symmetric deployment of some of the Lamb wave exciters in one Lamb wave exciter ring.

Figure 7:
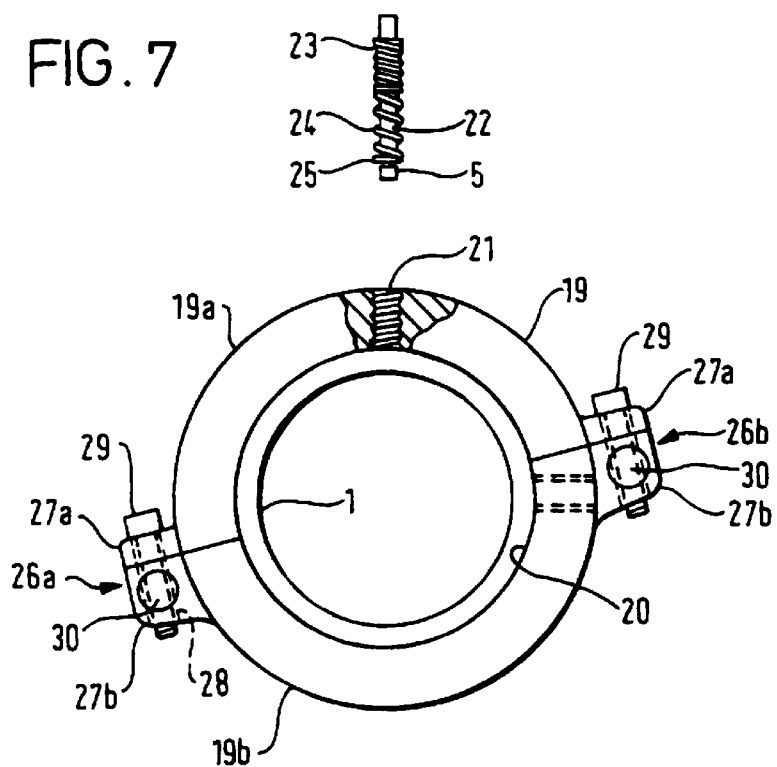
Figure 8:
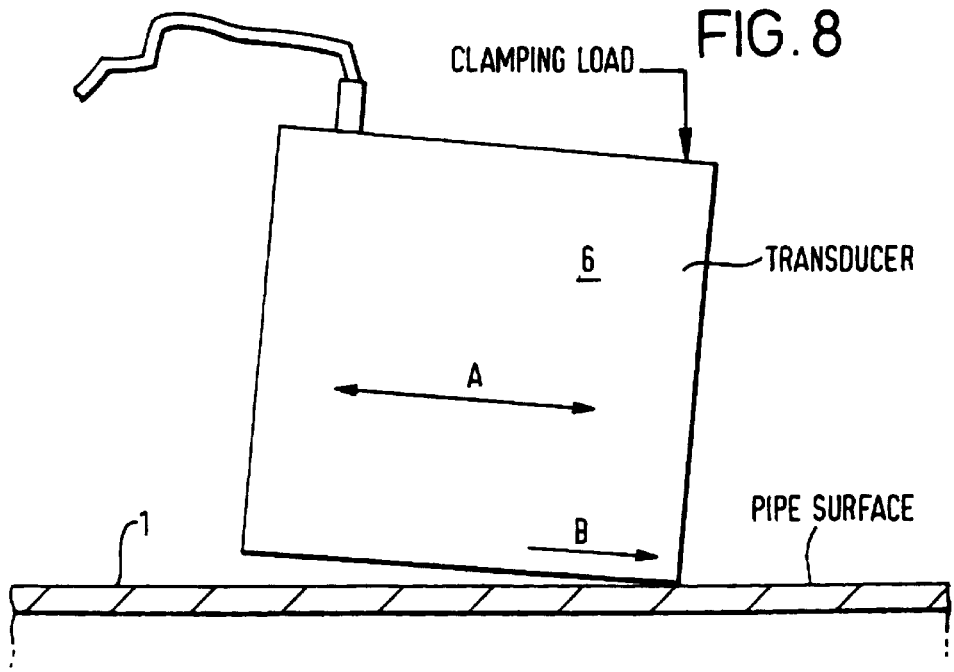
Figure 9:
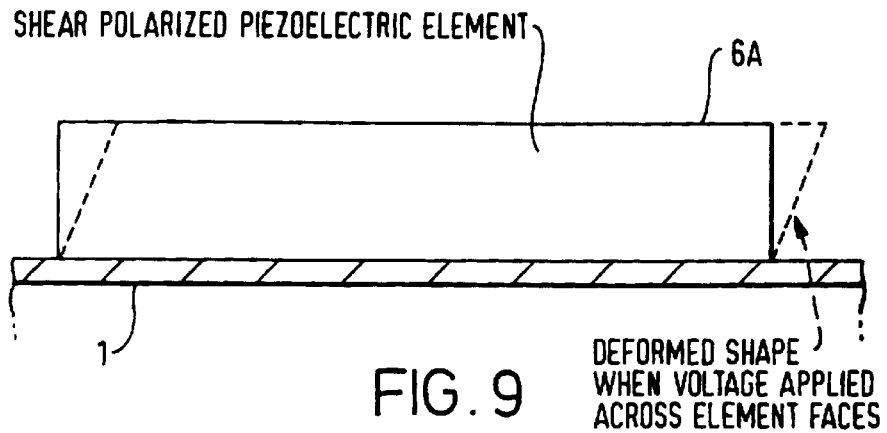
Figure 10A:
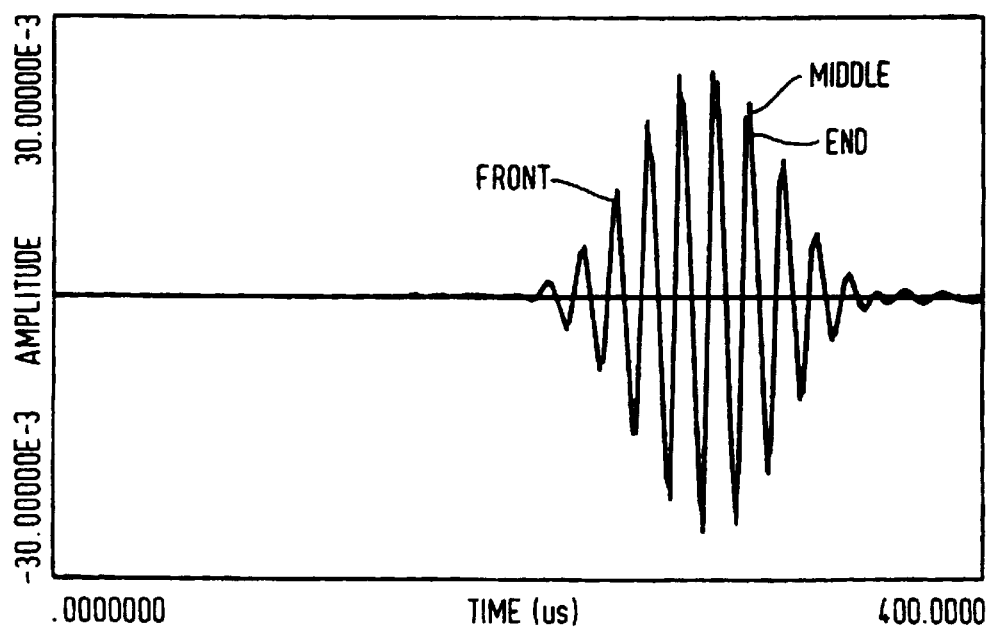
Figure 10B:
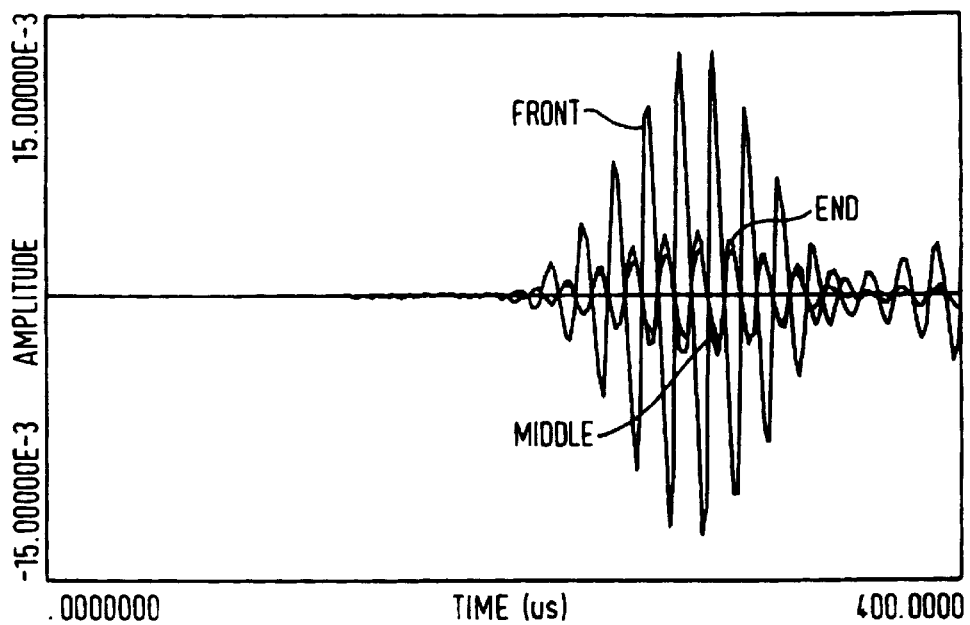
Figure 11:
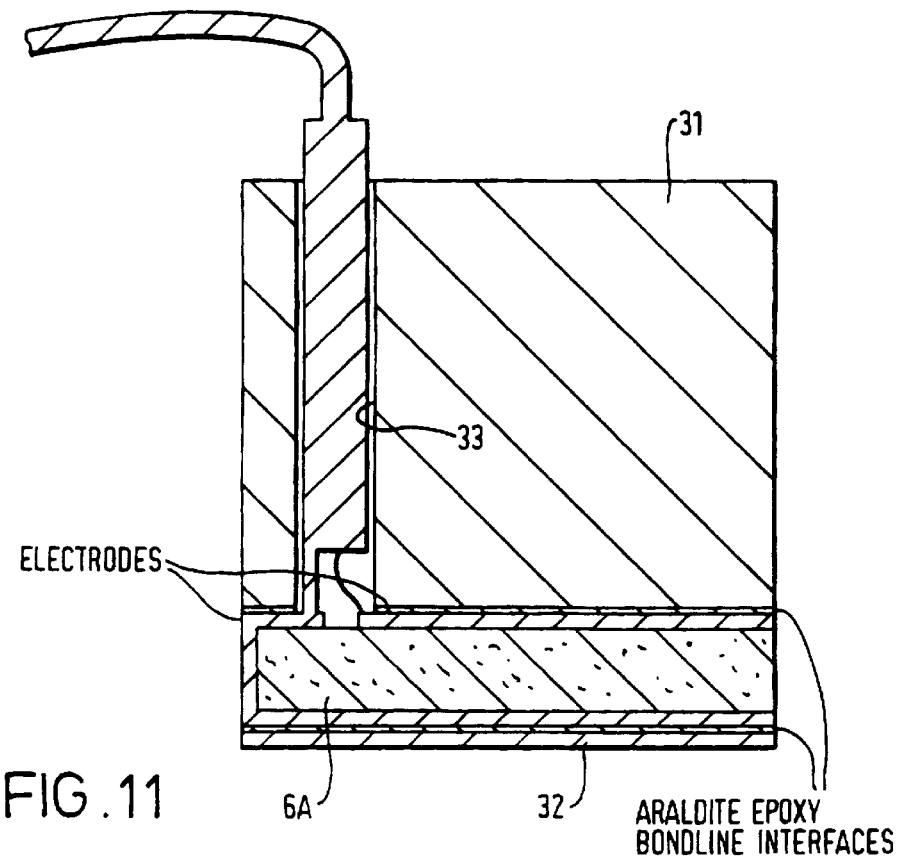

FIG. 7 shows a clamping means by which the excitation assembly can be secured to the pipe, FIG. 8 depicts an expansion transducer deployed using asymmetric load clamping means, FIG. 9 illustrates the deformation of a shear polarised piezoelectric transducer, FIG. 10a portrays the signal received where a piezo electric shear transducer is used, FIG. 10b shows the signal received where an expansion transducer is used, and FIG. 11 depicts a second embodiment of a Lamb wave exciter.

FIG. 1 shows that at a desired operating frequency of 70 kHz the fastest propagation mode in a 76.2 mm diameter pipe with a wall thickness of 5.5 mm is the L(0,2) mode as opposed to the L(0,1) mode and it is this Lamb wave mode which is used to inspect the pipe. The L(0,1) and L(0,2) wave modes are differently propagating axi-symmetric wave modes. The difference between them is in the distribution of displacements and stresses through the pipe. The terminology is more fully explained in the article by M. G. Silk and K. F. Bainton in the journal "Ultrasonics" of January 1979 at pp 11–19 and entitled The propagation in metal tubing of ultrasonic wave modes equivalent to Lamb waves.

FIG. 2 shows a length of the pipe 1 to which a Lamb wave excitation assembly 2 of the apparatus is clamped. The excitation assembly 2 comprises a first excitation ring 3A (which is shown in more detail in FIG. 6) a second excitation ring 3B, and a third excitation ring 3C. Each ring is of similar construction to the ring 3A shown in FIG. 6.

The excitation rings 3A, 3B, 3C are each comprised of a set or belt of symmetrically deployed Lamb wave exciter/transducers 5, typically 16 for a 3 inch diameter pipe and 32 for a 6 inch diameter pipe. The minimum number of Lamb wave exciters required in a ring is related to the highest order non-axisymmetric mode in the dispersion diagram at the highest frequency present in the excitation signal. If this mode order is say 13 then the minimum number of elements is 14. Each Lamb wave exciter comprises a high impedance piezoelectric element 6 and is illustrated in detail in FIGS. 4 and 5 or 11. In use each of the Lamb wave exciters is pressed into operative engagement with the surface of the pipe 1 by a clamping means which for this example of the apparatus applies a load of 40 N to every one of the exciters. This arrangement provides sufficient coupling between the pipe 1 and the exciters 5 to make a coupling fluid unnecessary.

An example of a suitable clamping means is shown in FIG. 7. This clamping means consists of a ring 19 having an internal aperture 20. Spacer means such as three radially extending screws (not shown) are located at 120° intervals around the ring 19. The screws are adjustable to engage the pipe wall and support the ring coaxially around the pipe so that it is spaced from the pipe. This minimises contact with the pipe, and hence minimises any damping of the desired waves and also reduces any wave reflection caused by the clamping means. A plurality of radially extending through holes 21 are equiangularly spaced around the ring 19. Sufficient through holes 21 are provided to enable the required number of Lamb wave exciters 5 to be mounted one in each through hole 21. Each Lamb wave exciter 5 is mounted on the end of an elongate push rod 22. The push rod 22 is slidably received into an externally threaded sleeve 23 so that a compression coil spring 24 acting between the sleeve 23 and an abutment 25 on the rod 22 tends to project the rod 22 longitudinally. The Lamb wave exciter 5 is installed in the clamping means by screwing the sleeve 23 into the internally threaded hole 21 so that the Lamb wave exciter 5 is pressed against the exterior of the wall of the pipe 1 by the action of the spring 24. The load can be adjusted by screwing and unscrewing the sleeve 23.

In a preferred form of the clamping means, the ring 19 is split radially into one or more separable parts 19a, 19b. In the example illustrated in FIG. 7 the two parts 19a, 19b, are joined together by two hinge and bolt assemblies generally designated at 26a and 26b. Each hinge and bolt assembly comprises a pair of brackets 27a, 27b. The bracket 27a being mounted on a first part of the ring 19 adjacent where the ring is split, and each bracket 27b being similarly mounted upon the other ring part 19b.

One of the brackets 27a has a through hole 28 in it which extends tangentially to the ring and is of sufficient diameter for an allen key bolt 29 to be received through it. The through hole 28 is not threaded. Each bracket 27b also includes a tangentially extending aperture into which the bolt 29 is received. The bolt 29 screws into a pivot pin 30 mounted to extend parallel to the axis of the ring 19. The aperture in each bracket 27b allows the bolt 29 to pivot when it is screwed into the pivot pin 30.

The bracket 27a in the assembly 26b differs from the one in the assembly 26a in that the bracket 27a consists of two forks which allow the bolt 29 to be swung out from the bracket when loosened so allowing the ring parts 19a, 19b to be hinged apart around the pivot pin 27b in the other of the brackets.

Although the preferred form of mounting means is the hinged split ring described, it is possible to use a simple ring slipped onto the end of the pipe or a split ring without the hinge and bolt assemblies described but with simple bolt together brackets, overlooking fastenings, buckle and belt type fastenings and a wide range of other mechanisms. The ring shaped mounting means is preferred but any structure which will take up a ring like shape and provide support for the Lamb wave exciters may be suitable, for example, a polygonal structure or an articulated belt structure.

A detailed section through one of the expander type exciter elements is shown in FIGS. 4 and 5. The piezoelectric element 6 is elongate and polarised so that it expands and contracts along its length. Elements of this type are known for use as strain gauges. The element 6 has a backing structure comprising a casing 7, fabricated from Tufnel, in the base of which it is housed. The casing has upright opposing side walls 8 and end walls 9 and a sealing cover 10. A miniature coaxial cable 11, for connection of the piezoelectric element 6 to control and analysis instrumentation, penetrates the cover 10 and is connected with the piezolelectric element 6 within a chamber 12 formed by the casing. A thin face plate shim 13 is secured against the face of the piezoelectric element 6 to provide a wear plate which protects the piezoelectric element 6 so as to freely transmit forces from the pipe to the piezoelectric element. The shim 13 must be sufficiently thin that its shear stiffness is high enough not to interfere with the coupling of the piezoelectric element 6 with the pipe 1. In the embodiment the shim is of 0.06 mm thick steel or brass and may be electrically insulated from the piezoelectric element at the bondline between them. However, the shim 13 may be of a non-conducting material to electrically insulate the piezoelectric element 5. The chamber 12 is filled with tungsten loaded epoxy which is a lossy material serving the purposes of protecting the gauge and electrical connections, providing flexural stiffness so that the very brittle piezoelectric element 6 is not damaged when pressed against a rough pipe surface and it damps out reverberations so that the transducer outputs a faithful reproduction of an excitation signal applied to it or, when used as a receiver, it generates a voltage corresponding to a wave passing it. Thus the lossy material provides means to accommodate pipe surface roughness and to damp out reverberations.

FIG. 9 diagrammatically shows a shear polarised piezo electric transducer 6A which may be used in preference to the expansion type piezo electric transducer 6. With this type of transducer the face engaging the pipe wall moves in one direction only parallel to the pipe axis and so exerts a force in the same direction over its full length. FIGS. 10a and 10b illustrate the improvement achieved in signal clarity when a shear polarised transducer is used. FIG. 10a shows the received signal obtained with a single shear polarised transducer loaded at three different positions along its length. It can be seen that the magnitude of the response is similar at the three positions and, crucially the phase is the same. FIG. 10b shows the result of a similar experiment with an expansion type transducer where clear phase changes can be seen. The experiments were with a single transducer instead of a ring so that a significant amplitude of non axially symmetric modes can be seen.

FIG. 11 shows a second embodiment of a single Lamb wave exciter for use in an excitation ring. In this embodiment the shear polarised piezoelectric element 6A as described above, is adhesively bonded to a rigid block 31. In this case the rigid block 31 is made of steel and the bonding is achieved by an epoxy cement. A face shim 32, which may be made of brass, is bonded to the face of the piezoelectric element 6A. A passage 33 is formed through the backing block 31 and provides protective support for the electrical connections to the piezo electric element 6A. The rigid block backing structure can usefully back the expansion type piezoelectric element.

Each Lamb wave exciter ring 3 is controlled via the instrumentation shown in FIG. 3 so that each of the exciters 6 in any one exciter ring 3 act in phase. The instrumentation comprises a computer, which in this case is a personal computer 14 which computes the necessary, excitation signals for each exciter ring 3A, 3B, 3C. The excitation signals are then fed to a multi-channel signal generator 15 which in the embodiment described has three channels to supply signals to each of the excitation rings 3A, 3B, 3C. The signal generator 15 will have sufficient channels to supply as many excitation rings as are desired. More than three rings may be desired in some circumstances, e.g., to amplify the desired single mode Lamb wave. The excitation signals are then fed to an amplifier 16 which amplifies each channel of the excitation signals separately and applies them to the excitation rings 3 so that the excitation assembly generates a signal L(0,2) axi-symmetric mode Lamb wave propagating in one direction down the pipe.

In some applications modes other than the L(0,2) mode may be employed.

Different numbers of exciter rings 3 may be employed in order to suppress undesired axi-symmetric modes and to limit the propagation of the desired mode to one direction. In the currently preferred format, three rings are employed, successive rings being separated by a distance L as shown in FIG. 2. This distance L is set to be:

$$L = \frac{(2m+1)\lambda_1}{2}, m \text{ is integer}$$

where $\lambda_1$ is the wavelength of the mode which is to be suppressed in both directions. In the preferred format, m=0 so $$L = \frac{\lambda_1}{2}$$

However, due to the physical size of the rings, it is not always possible to achieve separations small enough to implement this, so m may be set to a larger integer.

The signal applied to the first exciter ring 3A is a toneburst centred on the desired frequency (commonly around 70 kHz) enclosed in a Hanning or Gaussian window to limit the bandwidth. The signal applied to the third ring 3C is identical to that applied to ring 3A but delayed by a time T given by:

$$T = \frac{\pi}{\omega}\left((2n+1) - \frac{\lambda_1}{\lambda_2}\right), \ n \text{ is integer}$$

where ω is the centre frequency of the toneburst (expressed in rad/sec) and $\lambda_1$ and $\lambda_2$ are the wavelengths at the centre frequency of the mode which is to be suppressed in both directions and the desired mode which is to be suppressed in the backward direction respectively. Generally, n is set to zero so:

$$T = \frac{\pi}{\omega}\left(1 - \frac{\lambda_1}{\lambda_2}\right)$$

The signal applied to the middle exciter ring 3B is the sum of the signals applied to rings 3A and 3C.

This arrangement suppresses the undesired mode in both directions at the centre frequency of the input toneburst, but not at the other frequencies present in the signal. If the desired mode is non dispersive (ie its velocity does not vary with frequency) then propagation of this mode in the backward direction is suppressed at all frequencies present in the input toneburst. However, if the mode is dispersive then suppression in the backward direction is only achieved at the centre frequency. In this case, it is desirable to modify the signal applied to the third ring 3C.

Suppose that the phase velocity of the desired mode is a function of frequency, $c=g(\omega)$. Then the wavelength, $\lambda$ is given by $$\frac{2\pi C}{\omega} = \frac{2\pi g(\omega)}{\omega}$$

Suppose that the excitation signal applied to the first ring is x(t) and the Fourier transform of this signal is $X(\omega)e^{i\omega t}$. At each frequency we want the excitation signal applied to the second ring to lag that applied to the first ring by T where $$T = \frac{\pi}{\omega} - \frac{L}{g(\omega)}$$

and L is the spacing between the exciter rings. Then the Fourier components of the required signal are given by $$Y(\omega)=X(\omega)e^{i\omega(t-T)}$$

and the excitation signal applied to the second ring is given by the inverse Fourier transform of Y(t), $$Y(t)=\int Y(\omega)e^{i\omega t}d\omega$$

where the integral is taken over the full bandwidth of the signal.

The signal applied to ring 3B will again be the sum of the signals applied to rings 3A and 3C. A similar procedure may used in reception to improve the analysis of received signals comprising a dispersive mode.

The cancellation of more than one unwanted axi-symmetric mode requires additional excitation rings. Additional excitation rings may also be useful for increasing the amplitude of the desired single axi-symmetric mode in the forward direction.

If the only object of using more than one exciter ring is to suppress backward propagation of the mode we wish to excite in the forward direction then it is advantageous to let $L=\lambda/4$. Then, T is a quarter period at the centre frequency of the excitation signal and it may be shown that the amplitude of the forward propagating wave is maximised at this frequency.

In the embodiment the excitation elements also serve as receivers, thus a Lamb wave that has been propagated down the pipe 1 and reflected back up the pipe 1 disturbs the piezoelectric elements of each Lamb wave exciter in the exciter rings 3. This disturbance causes the piezoelectric elements to generate a voltage signal which is applied to the instrumentation shown on the right in FIG. 3. Thus each exciter ring 3 generates a corresponding signal. Each of these signals is fed, one each to each one of an array 17 of high bypass filters and then to a receiver amplifier 18 before being supplied to a digital to analogue converter 19 and then to the computer 14 for analysis. The high bypass filters may be set at 10 kHz.

The signals received at each ring may be processed in software using an analysis similar to that used to produce the excitation signals for single mode, single direction propagation. The output of this processing is a signal comprising a single, axi-symmetric mode generated by reflections from features in the pipe. It is also possible to employ one receiver channel per Lamb wave exciter/transducer, rather than one per ring. If this is done it is possible to employ a more sophisticated analysis to determine the amplitudes of other, non-axisymmetric modes present in the reflected signal which may be produced by mode conversion at features in the pipe. One way of carrying out this analysis is described in: Alleyn D. N., and Cawley P., 'A 2-dimensional Fourier transform method for the measurement of propagating multi-mode signals', J Acoust Soc Am, Vol 89, pp1159–1168, 1991. This more sophisticated process can give more information about the nature and size of features in the pipe.

FIG. 8 diagrams an expansion type piezoelectric transducer element 6 in which the clamping load is applied to the front edge of the transducer element.

What is claimed is:

1. An apparatus for inspecting a pipe comprising:
   a first excitation ring;
   a second excitation ring, the first and second excitation rings being adapted to be secured to an exterior wall of a pipe;
   a plurality of angularly spaced wave exciters secured to each of the excitation rings, each wave exciter being controlled to induce a propagation, in a single direction along the pipe, of one of:
   (a) a single mode axially symmetric Lamb wave,
   (b) a single torsional mode wave, and
   (c) a single flexural mode wave;
   receiving means for receiving a wave; and
   analyzing means for analyzing the received wave and assessing a condition of the pipe.

2. A pipe inspection apparatus, comprising:
   a first excitation ring;
   a second excitation ring, the first and second excitation rings being adapted to be secured to an exterior wall of a pipe;
   a plurality of angularly spaced wave exciters secured to each of the excitation rings, each wave exciter being controlled to induce a single mode propagation along the pipe of one of:
   (a) a single mode axially symmetric Lamb wave,
   (b) a single torsional mode wave, and
   (c) a single flexural mode wave,
   each of the exciters also receiving one of the propagated waves; and
   analyzing means for analyzing the received waves and assessing a condition of the pipe.

3. The apparatus according to claim 1, further comprising:
   a third excitation ring, controlled in cooperation with the first and second excitation rings, for suppressing a propagation of unwanted modes of the waves and a propagation of the received wave in a reverse direction along the pipe.

4. The apparatus according to claim 3, wherein the receiving means includes at least one of the excitation rings.

5. The apparatus according to claim 3, wherein the plurality of wave exciters in each ring are supported in an equiangularly spaced relation for engagement with the pipe wall by a respective clamping member.

6. The apparatus according to claim 5, wherein:
each of the clamping members comprises a ring having an internal diameter spaced from the exterior wall of the pipe when clamped thereto;
a plurality of spacers, engageable between the ring and the exterior wall of the pipe, for securing the ring in a coaxially spaced relation around the exterior wall of the pipe; and
said wave exciters are equiangularly spaced around the ring and engage the exterior wall of the pipe.

7. The apparatus according to claim 6, wherein, in use, the clamping members apply a uniform force to each of the wave exciters to press each of the wave exciters against the exterior wall of the pipe with a same force.

8. The apparatus according to claim 6, wherein the ring is split in a radial direction for allowing the ring to be located around the pipe.

9. The apparatus according to claim 6, further comprising instrumentation for controlling the wave exciters in any one of the rings to act in phase.

10. The apparatus according to claim 5, wherein each said exciter is in communication with a corresponding channel of the analyzing means whereby non-axisymmetric modes of the waves are received for analysis.

11. A method of inspecting a pipe, comprising the steps of:
inducing a propagation, in one longitudinal direction of the pipe,
(a) a single mode axially symmetric Lamb wave,
(b) a single torsional mode wave, and
(c) a single flexural mode wave;
suppressing all but the single mode of the Lamb wave propagating in either longitudinal direction along the pipe;
suppressing the propagation of any Lamb wave in one longitudinal direction of the pipe;
receiving the propagated wave; and
analyzing said wave for identifying structures in the pipe, a condition of the pipe being determined as a function of the identified structures.

12. The apparatus according to claim 5, wherein a plurality of wave exciter/transducers are equiangularly spaced around the pipe under inspection, each of the exciters being in communication with a corresponding channel of the analyzing means whereby non-axisymmetric modes of the waves are received for analysis.

13. The apparatus according to claim 12, wherein each of the wave exciter/transducers comprises:
a shear polarized piezoelectric element, which deforms when a voltage is applied across its faces.

14. The apparatus according to claim 12, wherein each of the wave exciter/transducers comprises:
a piezoelectric element having a backing structure provided by a rigid backing block.

15. The apparatus according to claim 12, wherein each of the wave exciter/transducers comprises:
a piezoelectric element having a pipe engageable face protected by a face shim secured to the piezoelectric element.

16. The pipe inspection apparatus as set forth in claim 2, wherein the analyzing means sums the received waves for assessing the condition of the pipe.

17. The apparatus according to claim 12, wherein:
each wave exciter/transducer comprises a piezoelectric element polarized to deform when a voltage is applied across faces of the piezoelectric element; and
each of the piezoelectric elements includes a backing structure engageable by the means to clamp the piezoelectric element to the pipe, whereby a wave is propagated in the pipe in response to a control signal and a wave signal is generated in accordance with a wave traveling through the pipe.

18. The pipe inspections apparatus as set forth in claim 16, wherein analyzing means determines amplitudes of the axially symmetric wave as a function of the respective sums.

* * * * *